United States Patent [19]

Mitschke et al.

[11] 4,246,206
[45] Jan. 20, 1981

[54] PROCESS FOR THE PREPARATION OF N,N-BIS-(2-HYDROXYALKYL)-AMINOMETHANE PHOSPHONIC ACID DIMETHYL ESTER

[75] Inventors: Karl-Heinz Mitschke, Odenthal; Manfred Kapps, Bergisch-Gladbach, both of Fed. Rep. of Germany

[73] Assignee: Bayer Aktiengesellschaft, Leverkusen, Fed. Rep. of Germany

[21] Appl. No.: 954,047

[22] Filed: Oct. 23, 1978

[30] Foreign Application Priority Data

Nov. 11, 1977 [DE] Fed. Rep. of Germany ....... 2750555

[51] Int. Cl.³ .................... C07F 9/40; C08G 18/28
[52] U.S. Cl. .................................. 260/970; 528/72
[58] Field of Search ........................................ 260/970

[56] References Cited

U.S. PATENT DOCUMENTS

| | | |
|---|---|---|
| 3,076,010 | 1/1963 | Beck et al. .................. 260/970 X |
| 3,297,796 | 1/1967 | Smith et al. ................. 260/970 X |
| 4,060,571 | 11/1977 | Kapps et al. ................ 260/970 X |

OTHER PUBLICATIONS

Nachod et al., "Ion Exchange Technology", Academic Press Inc., N.Y., (1956), p. 12.

*Primary Examiner*—Anton H. Sutto
*Attorney, Agent, or Firm*—Gene Harsh; Joseph C. Gil

[57] ABSTRACT

The invention relates to a process for the preparation of N,N-bis-(2-hydroxyalkyl)-aminomethane phosphonic acid dimethyl esters corresponding to the following general formula:

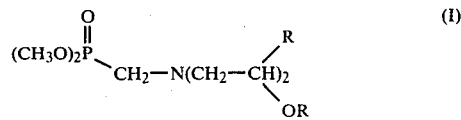

wherein each R, may be the same or different and represents hydrogen or, preferably, a lower, linear or branched alkyl radical or halogen-substituted alkyl radical containing from 1 to 6 carbon atoms.

4 Claims, No Drawings

PROCESS FOR THE PREPARATION OF N,N-BIS-(2-HYDROXYALKYL)-AMINOMETHANE PHOSPHONIC ACID DIMETHYL ESTER

BACKGROUND OF THE INVENTION

Although compounds corresponding to formula (I) above, which are primarily used as flame-retarding additives for plastics, particularly polyurethanes, have been mentioned in connection with higher homologues of this class of compounds, the preparation thereof by known methods does not give satisfactory results (cf., for example, U.S. Pat. Nos. 3,076,010 and 3,297,796). For example, only the diethyl esters of bis-(hydroxyethyl)-aminomethane phosphonic acid have hitherto been available, being produced by reacting diethanolamine with aqueous formaldehyde and diethyl phosphate (cf., for example, German Auslegeschrift No. 1,143,022). So far it has not been possible to satisfactorily produce the corresponding dimethyl esters which, of course, would be of considerable interest.

Where compounds corresponding to the above formula are produced by conventional processes, secondary reactions occur to a considerable extent. Reference has been made in the literature, inter alia, to the alkylating effect of, in particular, lower alkyl phosphites, but also of dimethyl phosphonates on amines (Houben-Weyl, Methoden der organischen Chemie, Vol. 12/2, page 10 and Vol. 12/1, page 411).

The same occurs in the reaction of alkanolamines and formalin with dimethyl phosphite. In addition, the water present in the reaction of dialkanolamine and formalin hydrolyzes the phosphite component which, as a result, may no longer participate in the required reaction. Another secondary reaction is the transesterification of the methoxy group bound to the phosphorus with the terminal hydroxyl groups in the alkanolamine. The transesterification reaction is known to be promoted to a greater extent in the case of phosphites containing methyl groups than in the case of higher homologues.

DESCRIPTION OF THE INVENTION

The present invention relates to a process for the preparation of N,N-bis-(2-hydroxyalkyl)-aminomethane phosphonic acid dimethyl esters corresponding to the following general formula:

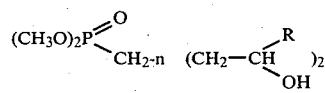

wherein each R may be the same or different and represents hydrogen or, preferably, a lower, linear or branched alkyl radical or halogen-substituted alkyl radical containing from 1 to 6 carbon atoms; comprising reacting oxazolidines corresponding to the following general formula:

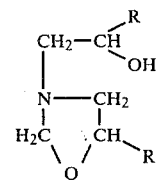

wherein R is as defined in connection with general formula (I); with dimethyl phosphite in the presence of H-acid compounds.

It has surprisingly been found that N,N-bis-(2-hydroxyalkyl)-aminomethane phosphonic acid dimethyl esters corresponding to general formula (I) may be quickly produced in hitherto unattainable yields providing the reaction in question is carried out in the presence of H-acid compounds.

The process according to the present invention may be carried out both continuously, generally in several stages in a reaction cascade, and in batches.

Where the process according to the present invention is carried out in batches, the dimethyl phosphite is preferably initially introduced together with the H-acid compound, followed by the addition of compound (II). However, it is also possible initially to introduce the dimethyl phosphite on its own and then to add compound (II) together with the H-acid compound. Depending upon the size of the radical R in compound (II), the reaction temperatures are from 0° to 100° C., preferably from 20° to 60° C., while the reaction times amount to between 0.5 and 6 hours, preferably between 1 and 4 hours. The reaction is preferably carried out in the absence of solvents, although it is also possible to use suitable solvents, such as benzene, toluene or petroleum ether.

After the components have been added, as noted above, the reaction mixture is preferably heated. The progress of the reaction may be followed by NMR spectroscopy. The reductions in the P-H-signal of the dimethyl phosphite and in the characteristic signals of compound (II) are a measure of the conversion level of the reaction. In addition, the level of secondary reactions (transesterification, alkylation, possible hydrolysis) may also be effectively monitored by NMR spectroscopy. The resulting compounds, particularly the dimethyl ester of N,N-bis-(2-hydroxypropyl)-aminomethane phosphonic acid, are colorless to pale yellow, clear liquids which are completely soluble in the conventional solvents.

According to the present invention, H-acid compounds are used as catalysts. Suitable H-acid compounds are inorganic and organic monofunctional and polyfunctional acids. Examples include sulphuric acid, hydrochloric acid, nitric acid and phosphoric acid; monocarboxylic and polycarboxylic acids, such as acetic acid, chloroacetic acid, benzoic acid, salicylic acid, oxalic acid, malonic acid and phthalic acid; sulphonic acids, such as alkyl and aryl sulphonic acids; phosphonic and phosphinic acids, such as alkyl and aryl phosphonic and phosphinic acids; phenols; and derivatives thereof, such as partial esters and amides of phosphoric acid, phosphonic acid and polycarboxylic acids.

It is also possible to use combinations of H-acid compounds with one another or even mixtures of acids with acidic ion exchange materials.

Particularly effective H-acid compounds are those having a pK$_s$-value of from about −3 to 10, and preferably from 1 to 6 (the pK$_s$-values are based on values in aqueous medium). It is particularly preferred to use compounds containing phosphorus.

The H-acid compounds are preferably used in anhydrous form. They are used in quantities of from 0.1 to 25 mol %, preferably from 2 to 15 mol %, based on the end product, depending upon molecular weight and H-functionality. Although it is in principle possible to use larger quantities, it is not advisable to do so because of the resultant reduction in the pH value of the reaction mixture.

The oxazolidines of formula (II) used are preferred formed from bis-(2-hydroxyalkyl)-amines and formaldehyde, the formaldehyde preferably being introduced first of all, followed by addition of the dialkanolamine at from about 40° to 50° C. Suitable alkanolamines include, for example, diethanolamine, diisopropanolamine or other corresponding amines. Before they are used, the oxazolidines are, where possible, dehydrated or distilled.

By following the process of the present invention, it is possible for the first time to synthesize the methyl homologues, on which the class of compounds corresponding to formula (I) are based, in high purity and yields. Accordingly, it is also possible to produce compounds which contain terminal secondary hydroxyl groups and hence to obtain end products of improved, uniform quality where foaming is carried out with polyols and diisocyanates as compared to compounds produced by conventional processes. This result is attributable to the absence of secondary products formed by hydrolysis, transesterification or alkylation and to unreacted starting materials. These findings are confirmed by NMR spectroscopy.

In general, the H-acid compounds added in accordance with the present invention may remain in the reaction products and are thus used, for example, as flameproofing agents together with the ester of formula I. It is also possible, however, to convert the H-acid fractions, for example, into the corresponding alkali metal salts thereof and then to remove them by extraction. The esters may thus be isolated in this way.

The process according to the present invention is illustrated by the following Examples in which the percentages quoted represent percent by weight, unless otherwise indicated.

EXAMPLES

Production of the oxazolidines corresponding to formula II (a) 29.5 kg (363 mols) of a 37% aqueous solution of formaldehyde were initially introduced into a reaction vessel and preheated to approximately 40° C., followed by the addition over a period of 3 hours of 47.9 kg (360 mols) of molten diisopropanolamine (by the addition of approximately 5% of water, diisopropanolamine remains liquid at room temperature) at such a rate that the internal temperature remained at from 40° to 43° C., optionally with cooling. After the addition, the reaction mixture was stirred for about 1 hour at 50° C. The resulting oxazolidine of formula II (R=CH$_3$) was dehydrated in the steam jet vacuum (without a column in between) over a period of 5.5 hours at a temperature of 80° C. falling to 60° C. towards the end of dehydration. 50.6 kg (96.5% of the theoretical yield) of product having a purity of 99.85% (GC) and a water content of approximately 0.1% were obtained.

(b) 1670 g (95% of the theoretical yield) of the oxazolidine of formula II (R=H) having a purity of 96.8% (GC) were similarly obtained from 1230 g (15.15 mol) of a 37% aqueous solution of formaldehyde and 1577 g (15 mols) of diethanolamine.

EXAMPLE 1

33 kg (300 mols) of dimethyl phosphite and 2.91 kg of dibutyl phosphate were mixed in a reaction vessel and heated to from 40° to 42° C. 44.9 kg (309 mols) of the oxazolidine produced in accordance with (a) were introduced into this mixture over a period of 2.5 hours, the above-mentioned temperature being maintained by cooling. Towards the end of the addition, the temperature was slowly increased to 50° C., followed by stirring for about 3 hours. A pale yellow liquid having the following composition:

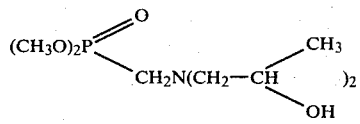

a density of 1.135 g/ml (25° C.) and a viscosity of 754 cP (25° C.) was obtained in a yield of 80.4 kg (99.5% of the theoretical yield). The product still contained 0.046 mol (per mol of the dimethyl compound) of

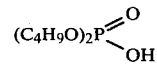

EXAMPLE 2

(Comparison, without H-acid compounds)

145.2 g (1 mol) of the oxazolidine produced in accordance with (a) were added dropwise over a period of 30 minutes at 40° C. to 110 g (1 mol) of dimethyl phosphite, followed by stirring for 3 hours at 50° C.

According to NMR measurements, approximately 13.5% of dimethyl phosphite, approximately 4.5% of desmethyl compound (formed by alkylation), approximately 12% of oxazolidine and approximately 6% of methanol were still present. Further heating did not complete the reaction, but instead increased the formation of secondary products and the rise in viscosity.

EXAMPLE 3

117 g (1 mol) of the oxazolidine produced in accordance with (b) were added over a period of 25 minutes with stirring and cooling to a mixture of 110 g (1 mol) of dimethyl phosphite and 7.9 g of dibutyl phosphate, followed by stirring for 3 hours at 40° C. A pale yellow liquid having the following composition:

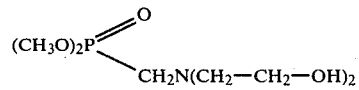

a density of 1.2259 g/ml (25° C.) and a viscosity of 350 cP/25° C.) was obtained in a quantitative yield.

EXAMPLE 4

(Comparison, without H-acid compounds)

117 g (1 mol) of the oxazolidine produced in accordance with (b) were added dropwise over a period of 25 minutes to 110 g (1 mol) of dimethyl phosphite, followed by stirring for 3 hours at 50° C.

According to NMR measurements, approximately 5.5 mol % of dimethyl phosphite, approximately 7.7 mol % of desmethyl compound (formed by alkylation), approximately 5 mol % of oxazolidine and approximately 7 mol % of methanol were still present. Further heating did not complete the reaction, but instead greatly increased the viscosity and darkened the color of the end product.

EXAMPLE 5

55 g (0.5 mol) of dimethyl phosphite and 3 g of chloromethane phosphonic acid were mixed, followed by the addition with stirring and cooling at 40° C. of 74.7 g (0.513 mol) of the oxazolidine produced in accordance with (a). The reaction mixture was then stirred for 3 hours at 50° C. A pale yellow liquid having the following composition:

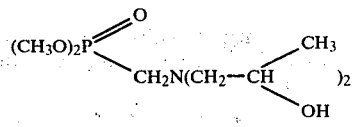

was obtained in a quantitative yield. The product still contained 0.044 mol of chloromethane phosphonic acid (per mol of the dimethyl compound). The chloromethane phosphonic acid may be converted into the corresponding sodium salt by adding twice the molar quantity of an aqueous NaOH solution. The product is extracted with toluene while the salt remains behind in the aqueous phase.

Both in the preceding Examples and in the following Examples, the catalyst was left behind in the reaction mixture.

EXAMPLE 6

Following the procedure of Example 5, a pale yellow liquid having the following composition:

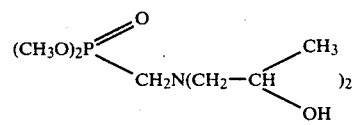

is obtained in a quantitative yield from 55 g (0.5 mol) of dimethyl phosphite, 2.8 g of tetramethylene phosphinic acid and 74.7 g (0.514 mol) of the oxazolidine produced in accordance with (a).

EXAMPLE 7

Following the procedure of Example 7, a pale yellow liquid having the following composition:

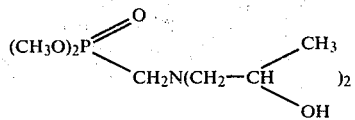

is obtained in a quantitative yield from 55 g (0.5 mol) of dimethyl phosphite, 2.4 g of vinyl phosphonic acid and 74.7 g (0.514 mol) of the oxazolidine produced in accordance with (a).

EXAMPLE 8

Following the procedure of Example 7, a pale yellow liquid having the following composition:

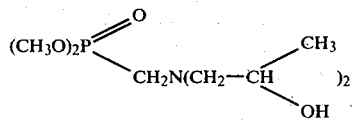

is obtained in a quantitative yield from 55 g (0.5 mol) of dimethyl phosphite, 4.9 g of p-toluene sulphonic acid and 74.7 g (0.514 mol) of the oxazolidine produced in accordance with (a).

EXAMPLE 9

Following the procedure of Example 5, a pale yellow liquid having the following composition:

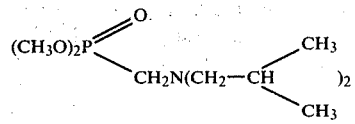

is obtained in a quantitative yield from 110 g (1 mol) of dimethyl phosphite, 8.8 g of phosphoric acid and 149.6 g (1.03 mol) of the oxazolidine produced in accordance with (a).

EXAMPLE 10

Following the procedure of Example 5, a mixture of 145.2 g (0.2 mol) of the oxazolidine produced in accordance with (a) and 7.6 g of glacial acetic acid was added dropwise at 40° C. to 110 g (1 mol) of dimethyl phosphite, followed by stirring for about 3 hours at 45° C. A pale yellow liquid having the following composition:

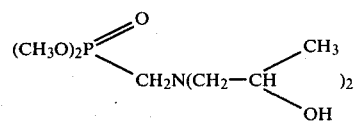

is obtained in a quantitative yield.

EXAMPLE 11

(The use of the product of Example 1 as a flameproofing agent in a rigid polyurethane foam)
Foaming formulation:
- 85 g of a polyether polyol obtained by the propoxylation of saccharose (OH-number 380; viscosity at 25° C., 13,000 mPas),
- 15 g of the product of Example 1,
- 1.5 g of a silicone stabilizer based on a polysiloxane modified with terminal polyether groups, 0.5 g of water,
2.0 g of dimethyl cyclohexylamine,
28.0 g of monofluorotrichloromethane,
115.0 g of crude 4,4'-diisocyanatodiphenyl methane.

Foaming:

The polyol was mixed by stirring with the product of Example 1, the additives and the blowing agent and the quantity of blowing agent volatilized during mixing was replaced. The isocyanate was then added and the mixture intensively stirred. All the components had been heated to 20° C.±0.5° C. before mixing. Immediately after mixing, the reaction mixture was poured into a mold of packing paper (base area 20×20 cm², height 14 cm). The cream time and the gel time were both measured during the foaming reaction; flammability was determined in accordance with ASTM. The following results were obtained:

Cream time [s]: 32
Gel time [s]: 145
Gross density [kg/m³]: 33.2
Compressive strength [MPa] (in the foaming direction): 0.24
Dimensional stability 5 h+100° C. [%, by volume]: no change
Flammability according to ASTM-D-1692
  length burned [cm]: 3.7 cm
  extinguishing time [s]: 35.

What is claimed is:

1. A process for the preparation of N,N-bis-(2-hydroxyalkyl)-aminomethane phosphonic acid dimethyl esters corresponding to the following general formula:

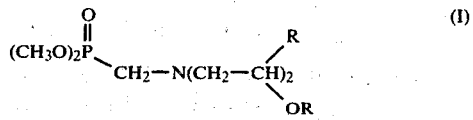

wherein each R may be the same or different and represents hydrogen or a linear or branched alkyl or halogen-substituted alkyl radical containing from 1 to 6 carbon atoms, comprising reacting oxazolidines corresponding to the following general formula:

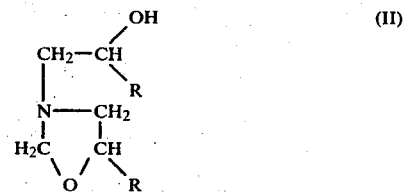

with dimethyl phosphite in the presence of H-acid compounds, said H-acid compounds being used in a quantity of from 2 to 25 mol percent based on the end product.

2. The process of claim 1, characterized in that the H-acid compound is used in a quantity of from 2 to 15 mol %, based on the end product.

3. A process as claimed in claim 1, characterized in that the reaction is carried out at a temperature of from 0° to 100° C.

4. A process as claimed in claim 1 or 2, characterized in that the reaction is carried out at a temperature of from 20° to 60° C.

* * * * *